United States Patent [19] [11] Patent Number: 4,953,550
Dunshee [45] Date of Patent: Sep. 4, 1990

[54] CHEMICAL THERMAL PACK HAVING AN OUTER POUCH PROVIDED WITH CAPILLARIES

[75] Inventor: Wayne K. Dunshee, St. Paul, Minn.

[73] Assignee: Minnesota Mining and Manufacturing Company, St. Paul, Minn.

[21] Appl. No.: 269,155

[22] Filed: Nov. 9, 1988

[51] Int. Cl.$^5$ .............................................. A61F 7/02
[52] U.S. Cl. ...................... 128/403; 62/530; 383/102
[58] Field of Search ............... 128/402, 403, 399, 379, 128/380, 82.1; 383/901, 100–103; 126/263, 204; 62/530, 4, 458; 206/219, 221, 222

[56] References Cited

U.S. PATENT DOCUMENTS

| | | | |
|---|---|---|---|
| 3,073,304 | 1/1963 | Schear | 128/156 |
| 3,175,558 | 3/1965 | Caillouette et al. | 128/403 |
| 3,302,501 | 2/1967 | Greene | 83/2 |
| 3,545,230 | 12/1970 | Morse | 62/530 |
| 3,643,665 | 2/1972 | Caillouette | 128/403 |
| 3,718,059 | 2/1973 | Clayton | 83/2 |
| 3,871,376 | 3/1975 | Kozak | 128/403 |
| 3,874,504 | 4/1975 | Verakas | 206/219 |
| 3,929,135 | 12/1975 | Thompson | 128/287 |
| 4,351,784 | 9/1982 | Thomas et al. | 264/22 |
| 4,404,820 | 9/1983 | Romaine | 62/530 |
| 4,456,570 | 6/1984 | Thomas et al. | 264/22 |
| 4,462,224 | 7/1984 | Dunshee et al. | 62/530 |
| 4,622,036 | 11/1986 | Goodrum | 604/367 |
| 4,688,572 | 8/1987 | Hubbard | 128/902 |
| 4,756,311 | 7/1988 | Francis, Jr. | 128/403 |

OTHER PUBLICATIONS

Package Instructions, Betty Crocker TM Oriental Classics TM Meal.

Primary Examiner—William H. Grieb
Assistant Examiner—M. Graham
Attorney, Agent, or Firm—Donald M. Sell; Walter N. Kirn; Dale A. Bjorkman

[57] ABSTRACT

This invention relates to hot or cold thermal packs having an outer pouch provided with capillaries to allow drainage of the pack and optionally to provide a temperature moderating effect.

23 Claims, 2 Drawing Sheets

CHEMICAL THERMAL PACK HAVING AN OUTER POUCH PROVIDED WITH CAPILLARIES

BACKGROUND OF THE INVENTION

This invention relates to chemical thermal packs. More specifically, this invention relates to hot or cold thermal packs of the type placed in contact with the body to relieve pain, reduce swelling and the like.

U.S. Pat. No. 3,175,558 to Caillouette et al. discloses a thermal therapeutic pack useful either as a heat pack or a cold pack wherein the bag that contains chemicals providing the thermal effect is insulated from the body by an absorbent material.

U.S. Pat. No. 3,874,504 to Verakas discloses a chemical thermal pack that consists of an outer pouch containing a thermal chemical containing inner bag and a slidably received insulation sheet. The outer pouch is preferably made from flexible, transparent plastic, such as polyethylene.

U.S. Pat. No. 4,462,224 to Dunshee et al. discloses an instant hot or cold, reusable cold pack that consists of three separate compartments. By mixing the contents of two of the compartments, the user initiates a thermal reaction providing either heat or cold therapy. After this reaction has run its course, the contents of the third compartment may be mixed with the first and second compartments to produce a gel that is relatively soft and moldable when frozen.

U.S. Pat. No. 4,756,311 to Francis, Jr. discloses a microwavable gel pack wherein the gel is contained in an envelope fabricated from a stretchable laminate having an inner layer of polyethylene or polyurethane and an outer layer of nylon, nylon sclair, paper or a fabric. The laminate materials must not allow rupture of the pack when subjected to microwave energy of approximately full power of a microwave heating device for a period of time exceeding about two minutes but not exceeding about four minutes.

U S. Pat. No. 3,929,135 to Thompson discloses a top sheet having tapered capillaries for use in absorptive devices such as diapers, sanitary napkins, bed pads, incontinent pads, towels, bandages and the like. Other liquid impermeable sheets that are merely perforated without adding appreciably to the thickness of the sheet, such as Delnet TM Sheeting (commercially available from Hercules Chemical Co., Wilmington, Del.), are used as non-stick layers over absorbent materials in such items as wound dressings.

SUMMARY OF THE INVENTION

This invention relates to a chemical thermal pack having a flexible liquid-tight inner bag containing a temperature-retaining composition. The bag is disposed within an outer pouch constructed at least partially from a sheet of liquid impermeable material provided with capillaries. Each capillary has a base in the plane of the sheet and an apex remote from the plane of the sheet.

The capillaries of the outer pouch of the chemical thermal pack provide means for draining off excess water which may surround the inner bag due to condensation when the pack is used as a cold pack, or from immersing the pack in boiled water in preparation for use as a hot pack. The capillaries of the outer pouch also optimally provide a thin layer of air insulation that moderates the amount of heat which is felt by the user of the bag and helps prevent burns or discomfort from excess heat or coldness. Additionally, this thin layer of insulation prevents wasteful heat loss in a hot pack or premature warming in a cold pack, thereby extending the period of time during which the pack is comfortable to use in heat or cold therapy.

The chemical thermal pack may additionally be provided with an insulation layer that is slidably received in the outer pouch as disclosed in U.S. Pat. No. 3,874,504 to Verakas, or that is integrally formed with the outer pouch or otherwise configured in the pack.

DETAILED DESCRIPTION

Figure 1:
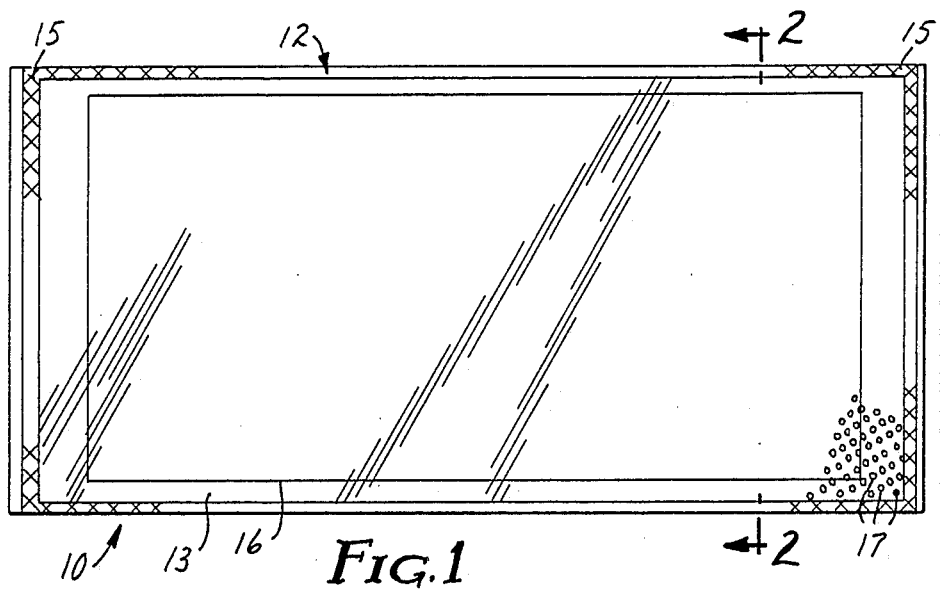
FIG. 1 is a plan view of a chemical thermal pack as used in this invention.
Figure 2:
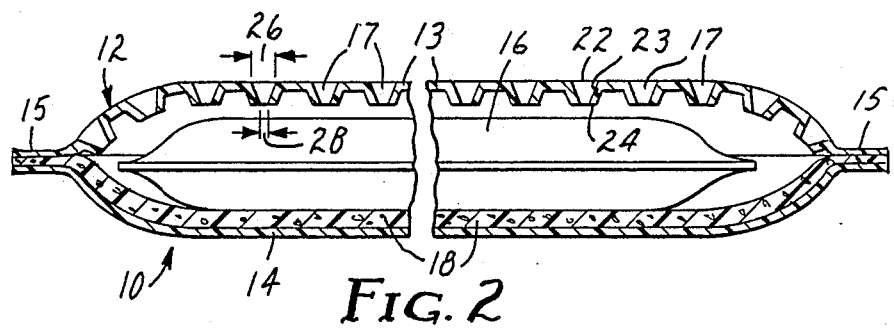
FIG. 2 is an enlarged cross-sectional view of the pack taken along the line 2—2 in FIG. 1 with parts thereof shown in elevation.

Turning now to the drawings, FIG. 1 and FIG. 2 show an embodiment of the chemical thermal pack 10 of this invention. Outer pouch 12 is constructed from a liquid impervious material, such as polyethylene, polyester, polypropylene, cellulose esters, cellulose ethers, nylon, polyvinyl alcohol acetals, polyvinyl chloride, polyvinyl chloride acetate, polystyral, methyl methacrylate and the like. This material may include other additives known in the art, such as a surfactant as disclosed in U.S. Pat. No. 4,456,570 to Thomas et al., or a coloring agent. The liquid impervious material may also be corona discharge surface treated as disclosed in U.S. Pat. No. 4,351,784 to Thomas et al., to increase the flow rate of liquid through the outer pouch and to improve adhesion of printed matter to the material. A preferred liquid impervious material is a medium density polyethylene sheet between about 0.0051 to about 0.0127 mm. thick.

In the embodiment as shown, outer pouch 12 consists of upper sheet 13 and lower sheet 14 that are bonded together by heat seal 15 on all four edges so as to form a closed pack.

Disposed within outer pouch 12 is chemical-containing inner bag 16 which holds any of the conventional temperature retaining compositions known in the art. Inner bag 16 is also prepared from a liquid impervious material, such as polyethylene, polyester, polypropylene, cellulose esters, cellulose ethers, nylon, polyvinyl alcohol acetals, polyvinyl chloride, polyvinyl chloride acetate, polystyral, methyl methacrylate and the like. A preferred inner bag 16 is constructed of laminate materials that are microwaveable, such as the polyethylene/nylon or nylon sclair laminate disclosed in U.S. Pat. No. 4,756,311.

Most preferably, inner bag 16 is constructed from a linear low density polyethylene/polyester laminate, such as ScotchPak TM Film, which is a 0.0254 mm. polyester/0.0635 mm. polyethylene laminate commercially available from 3M Company, St. Paul, Minn. A chemical thermal pack containing an inner bag constructed from ScotchPak ™ Film materials is heated at the 40% power setting ("defrost" setting) of the microwave. If an excessive amount of microwave energy is applied, the inner bag constructed from ScotchPak ™ Film will safely fail without explosion. The safe failure of inner bag 16 generally proceeds by excessive microwave heating of the gel so that the polyethylene seal surface is weakened to the point that inner bag 16 will not withstand stresses placed on the seal from expanding gasses. Before substantial pressure is built up, the sheets forming inner bag 16 peel apart at the heat seal and release contained gasses with an audible hiss and without expulsion of gel.

In the event of a catastrophic failure of inner bag 16 due to an excess of microwave energy, outer pouch 12 provides additional protection to the user. When inner bag 16 is constructed from laminates such as polyethylene/nylon or nylon sclair, excess microwave energy could result in explosion of inner bag 16, scattering hot gel over the microwave oven and potentially over the user. Capillaries 17 of outer pouch 12 allow the venting of expanding gasses from chemical thermal pack 10 while generally containing the hot gel. This effect is especially pronounced when capillaries 17 are directed inward, as discussed below. When inner bag 16 is constructed from ScotchPak ™ Film materials, the use of excess microwave energy results in a failure of the integrity of inner bag 16 in a less violent manner than the failure described above. Outer pouch 12 provides an additional layer through which such heated gel must pass before contacting the user.

The temperature-retaining composition may be, for example, a gel pack which when placed in a hot or cold environment retains the temperature of that environment for a suitable period of time following removal. In its most basic formulation, this gel pack contains only gelled water.

The temperature-retaining composition may alternatively be a multi-component system that is separated by a rupturable membrane. Upon mixing of the components, the composition either produces heat or absorbs heat, depending on the nature of the ingredients. An example of a heat producing composition is anhydrous magnesium sulfate as a principal constituent, as disclosed in U.S. Pat. No. 3,328,136. An alternative two component system for a hot pack would include calcium chloride as the heat producing powder and water as the solvent.

A two component heat-absorbing thermal pack is disclosed in U.S. Pat. No. 2,979,463 which has as its principal ingredient a urea or a urea compound along with ammonium chloride, potassium chloride or sodium chloride, and one or more heat insulation substances such as plaster of paris or asbestos. These components are mixed with water. In an alternative cold pack embodiment, ammonium nitrate may be used as the principal ingredient of a powder to be mixed with water.

In the embodiment of the invention as shown in FIGS. 1 and 2, insulation sheet 18 is heat-sealed together with upper sheet 13 and lower sheet 14 to integrally form outer pouch 12. Insulation sheet 18 may be of a fine cell or crosslinked polyethylene foam or other suitable material. Preferably, insulation sheet 18 does not absorb water. An example of a preferred material is a Polyfoam ™ closed cell polyethylene foam sheet commercially available from DuPont Co., Wilmington, Del.

Figure 3:
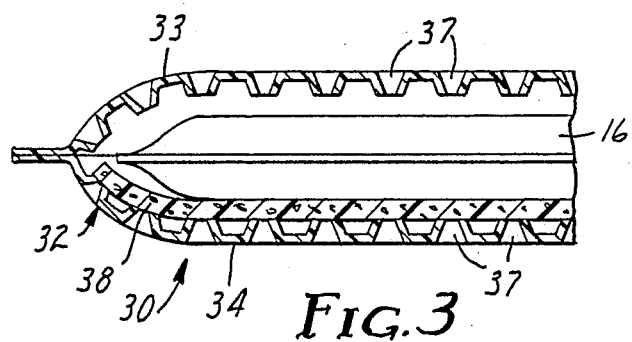
FIG. 3 is an enlarged cross-sectional view of an embodiment of this invention wherein the insulation layer is slidably received in the outer pouch.

In FIG. 2, a side view of capillaries 17 are shown. Each capillary 17 consists of a base 22 that is in the plane of upper sheet 13 and walls 23 terminating at apex 24. As shown in the figure, walls 23 are angled with respect to the plane of upper sheet 13 so that capillaries 17 are tapered. The angle of taper is shown in FIG. 3 of U.S. Pat. No. 3,929,135, incorporated herein by reference, as the angle alpha. The angle of taper suitable for use in the outer pouch of this invention is from about 0° to about 60°.

While capillary 17 as shown in the figures is generally in the form of a frustum of a conical surface, it is to be understood that any generally tapered structure, such as a frustum of a pyramid or the like with a triangular, square, or polygonal base, is within the contemplation of the invention. It is also to be understood that the tapered capillaries can be asymmetric (i.e., the angle of taper on one side can be different from that on another side) and that the angle of taper can change continuously (i.e., be curved) over the distance from base 22 to apex 24. In the latter case, the angle of taper is defined as the angle of the tangent to the side of the capillary at its point of minimum apex opening dimension. Also included in the term "tapered capillary" is a slot formed into upper sheet 13, said slot having finite length less than the width of upper sheet 13 and having its sides and ends tapered at angles analogous to those hereinafter described in relation to a circular tapered capillary. Also, as indicated above in the discussion of the angle alpha, walls 23 may be parallel so that capillaries 17 are not tapered.

Base opening dimension, except for the hereinbefore mentioned slot, is defined as the maximum open measurement in the plane of upper sheet 13 at capillary 17. Apex opening dimension, except for the hereinbefore mentioned slot, is defined as the maximum open measurement in the apex of capillary 17. When capillary 17 is in the form of a frustum of a conical surface, the base and apex opening dimensions are respectively base diameter 26 and apex diameter 28. Base diameter and apex diameter are hereinafter used interchangeably with, respectively, base opening dimension and apex opening dimension.

When capillary 17 is in the form of a slot having a finite length less than the width of the sheet, base opening dimension and apex opening dimension refer to the minimum open measurements in the base of the slot in the plane of sheet 21 and the apex of the slot remote from the plane of sheet 21, respectively. That is, base and apex opening dimensions refer to the widths rather than to the length of the slot.

Apex diameter 28 is from about 0.10 to about 2.54 mm., preferably from about 0.13 to about 0.51 mm. Base diameter 26 is within the range of about 0.15 to about 6.35 mm. Preferably base diameter 26 is within the range of about 0.2 to about 2.00 mm.

The height of capillary 17 is defined as the distance between the outermost surface of upper sheet 13 and apex 24. This height, of course, depends upon apex diameter 28, base diameter 26, and angle of taper alpha which have been selected as hereinbefore described. Capillary 17 should be of a height that provides a structure with a minimum tendency to collapse in use and which will provide an insulating layer of air between the underlying thermal pack and the user. The characteristics of the material of construction of upper sheet 13 in large measure determines suitable ranges for the height. When upper sheet 13 is medium density polyethylene of from about 0.0254 to about 0.0762 mm. thickness and apex diameter 28 and base diameter 26 are in the preferred range, and angle of taper alpha is in its critical range, the height of capillary 17 can be from about 0.04 to about 2.0 mm., more preferably from about 0.5 to about 1 mm., and most preferably about 0.6 mm. When capillary 17 is less than about 0.3 mm. high, little heat moderating effect is observed.

As shown in the figure, capillaries 17 are oriented on upper sheet 13 so that apex 24 points inward and the flat portion of upper sheet 13 contacts the user. Although the reversed orientation is permissible, the shown orientation is preferred because it affords a smooth surface to the user and provides an outwardly oriented smooth surface upon which instructions and similar matter may be printed.

FIG. 3 shows a chemical thermal pack 30 wherein insulation sheet 38 is slidably received in outer pouch 32, and thus is not heat sealed as an integral component of outer pouch 32.

In the embodiment as shown, outer pouch 32 is formed by heat sealing upper sheet 33 together with lower sheet 34, both of which are provided with capillaries 37.

Figure 4:
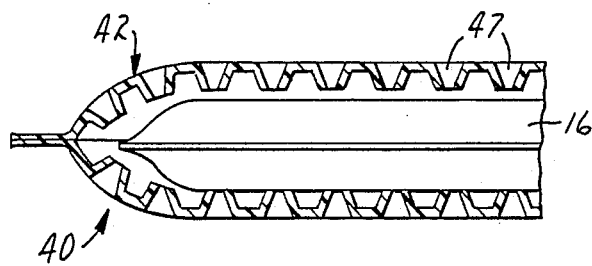
FIG. 4 is an enlarged cross-sectional view of an embodiment of this invention wherein capillaries are provided on both sheets of the outer pouch.

FIG. 4 shows a chemical thermal pack 40 that does not contain an insulation sheet. In this embodiment the entire outer pouch 42 is prepared from sheets containing capillaries 47. Because inner bag 46 is entirely enclosed by outer pouch 42 containing capillaries 47, inner bag 46 is insulated from melting contact with a hot pan when heated using the boiling water method. In this embodiment of the invention, chemical thermal pack 40 may actually be placed in a boiling pot of water without removal of the water from the heat source, as is required for other gel containing thermal packs.

Figure 5:
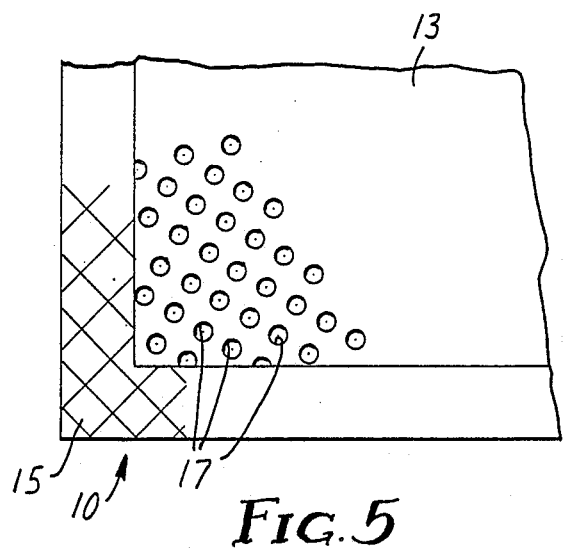
FIG. 5 is an enlarged plan view showing the pattern of capillaries in the outer pouch.

FIG. 5 is an enlarged plan view of chemical thermal pack 10, showing the pattern of capillaries 17 in outer pouch 12. A sufficient density of capillaries 17 is required to allow efficient drainage of the bag after being boiled in water, as well as an insulating layer of air. A preferred arrangement is where capillaries 17 as hereinbefore described are in an ordered arrangement with from about 5 to about 231 capillaries per square centimeter. More preferably, capillaries 17 are provided in an arrangement having about 50 to about 100 capillaries per square centimeter.

Liquid impermeable sheets provided with capillaries can be manufactured in any of several ways well known in the art. One particularly suitable method is to provide a heated mold with male elements of the shape and arrangement of the desired tapered capillaries (hereinafter a pin mold). Each male element is secured in such a fashion that its apex extends away from the base of the mold. A portion of liquid-impervious material is brought into contact with the heated mold between the mold and a resilient backing plate. Pressure is applied to the combination of mold, liquid-impervious material and resilient back plate and tapered capillaries are formed in the liquid-impervious material. An alternate way of constructing the sheet is to subject a portion of liquid-impervious material to vacuum forming over an appropriate mold by means well known in the art. A third way of making sheets for use in this invention is to cast the sheet on a mold designed for the purpose and similar to that previously described. After forming capillary structures in one of the three aforementioned ways, it may be necessary to physically remove material from the apex of the capillary structure so as to insure that the apex diameter is the desired value. Such removal of material can be accomplished by, for example, subjecting the apex to controlled abrasion or by heating the formed sheet so as to melt open the apex.

In order to contribute to a better understanding of this invention and not by way of limitation, the following examples are provided.

EXAMPLE 1

A 11.43 cm. by 25.4 cm. inner bag is constructed from a laminate of 0.0635 mm. linear low density polyethylene and 0.0254 mm. polyester, commercially available as ScotchPak ™ Film from 3M Company, St. Paul, Minn. Three hundred grams of a gel of the following formulation is placed in this inner bag, and the bag is closed by heat sealing. The gel contains by weight:

| | |
|---|---|
| Carbopol | .75% |
| Triethanolamine | .75% |
| Propylene Glycol | 10% |
| Quaternium 15 | 0.1% |
| Red Food Dye | .03% |
| Water | 88.37% |

The outer pouch is constructed from an upper sheet Vispore ™ X-6171 sheet material (commercially available from Visqueen Film Products Division of Ethyl Corporation, Richmond, Va.) and a lower sheet of matt embossed natural low density polyethylene film (commercially available from Bloomer Plastics, Bloomer, Wis.). These sheets are heat sealed together with a 10.15×25.4×0.1588 cm. insulation sheet of closed cell polyethylene foam sheet (commercially available as Microfoam ™ polypropylene foam sheeting from Amtek, Chadds Ford, Pa. to form an integral pouch with one open end. The inner bag is placed in the pouch between the Vispore ™ X-6171 sheet and the Polyfoam ™ insulation sheet and the open end is heat sealed closed. Heat sealing is performed on an impulse sealer, Audion Sealer Type SM420A (PAC Company, San Francisco).

The Vispore ™ X-6171 sheet used is a polyethylene film of about 0.0635 mm. thickness, having an ordered arrangement of about 83 capillaries per square centimeter. The capillaries are frustum of a conical surface having a base diameter of about 0.5 mm., an apex diameter of about 0.35 mm. and a distance of base to apex of about 0.6 mm.

EXAMPLE 2

A chemical thermal pack is constructed as in Example 1, except that the temperature-retaining gel is made of the following formulation:

| | |
|---|---|
| Methocal K15M | 5% |
| Propylene Glycol | 25% |
| Water | 69.97% |
| Red Food Dye | .03% |

EXAMPLE 3

A chemical thermal pack is prepared as in Example 1, except that the lower sheet of the outer pouch is also made from Vispore ™ X-6171sheet material.

EXAMPLE 4

A chemical thermal pack is prepared as in Example 3, except that no Polyfoam TM insulation sheet is provided.

EXAMPLE 5

The chemical thermal packs of Examples 1-4 are each placed in a microwave oven and heated at the defrost setting (40% power) for 2½ minutes. Each pack is found to provide a safe and pleasant delivery of heat therapy without discomfort from excessive heat.

EXAMPLE 6

The chemical thermal packs of Examples 1-4 are each immersed in about three quarts of boiling water after the pot was removed from the heat. After 7 minutes, each pack is removed from the water and placed upper sheet side down on a towel to allow the water to drain out. The chemical thermal packs are easily dried and each is found to provide a safe and pleasant delivery of heat therapy without discomfort from excessive heat.

EXAMPLE 7

A chemical thermal pack is prepared as in Example 1, except that the temperature-retaining gel is made of 70 weight percent water, 25 weight percent propylene glycol and 5 weight percent hydroxypropyl methylcellulose, type K15MDGS, as purchased from Dow Chemical Company, Midland, Mich. 48640 under the trademark "METHOCEL". The gel is made by first wetting the hydroxypropyl methylcellulose with the propylene glycol. The water is next added to form the finished gel. This pack is found to provide a pleasant delivery of cold therapy without discomfort from excessive coldness.

The temperature moderating effect of the capillary containing outer pouch of this invention can be observed in the side-by-side comparison as shown in the tables below.

Table 1 shows the skin temperatures observed on a human subject's calf being treated by test samples A, B and C, which are gel packs disposed within the outer pouch of this invention, and test sample D which is a gel pack disposed within an envelope made from a biaxially oriented nylon laminated to polyethylene (commercially available as Crown-lam 515 from Crown Zellerbach Division of James River Corp., San Francisco, Calif.) having an apparent thickness of 0.380 to 0.500 mm. The thermal packs were heated by immersion in boiled water or placing in a microwave oven at 40% power (defrost setting) for the time periods indicated on the table. N=1 or 5 indicates the number of trials performed on each sample.

A skin temperature of 112° F. is at or near the upper level of comfort for the subject. At a temperature of 120° F., some tissue damage occurs as a result of excessive heat. As the table reflects, the chemical thermal treatment pack having an outer pouch containing capillaries as herein disclosed (test samples A, B and C) maintains a moderated skin temperature near the upper level of comfort. A chemical thermal pack heated under the same conditions without a capillary containing outer pouch (test sample D) first exceeds the tissue damage level and then quickly drops below the desired temperature range for heat treatment. Indeed, at the three and six minute marks, the test became so painful that the subject had to remove the chemical thermal treatment pack.

TABLE I

| Time (Minutes) | Temperature °F. | | | |
|---|---|---|---|---|
| | A<br>Pack of Ex. 1<br>Boiling Water<br>10 Min. Submersion<br>(N = 1) | B<br>Pack of Ex. 1<br>Boiling Water<br>7 Min. Submersion<br>(N = 5) | C<br>Pack of Ex. 1<br>Microwave Oven<br>2.5 Min. at 40%<br>(N = 5) | D<br>Pack of Ex. 1<br>Pack Wrapped in Crown-lam 515<br>7 Min. Submersion<br>(N = 1) |
| 0.5 | 107.9 | 113.3 | 110.0 | 113.0 |
| 1.0 | 113.7 | 114.2 | 112.9 | 125.0 |
| 1.5 | 115.6 | 115.0 | 111.6 | 128.2 |
| 2.0 | 116.7 | 116.8 | 112.7 | 123.2 |
| 2.5 | 115.7 | 110.5 | 108.9 | 127.4 |
| 3.0 | 116.1 | 115.4 | 109.4 | 116.7 |
| 4.0 | 112.9 | 112.8 | 109.1 | 124.7 |
| 5.0 | 111.8 | 113.4 | 109.1 | 126.7 |
| 6.0 | 113.7 | 112.4 | 111.4 | 108.5 |
| 7.0 | 112.4 | 113.6 | 110.8 | 126.0 |
| 8.0 | 111.5 | 113.3 | 110.3 | 125.3 |
| 9.0 | 110.5 | 112.5 | 110.3 | 120.9 |
| 10.0 | 110.9 | 111.8 | 109.9 | 118.2 |
| 15.0 | 107.4 | 109.2 | 107.5 | 116.6 |
| 20.0 | 105.5 | 107.5 | 105.7 | 108.0 |
| 25.0 | 103.5 | 105.8 | 104.8 | 105.8 |
| 30.0 | 102.2 | 105.4 | 103.9 | 104.4 |
| 35.0 | 101.3 | 104.2 | 103.2 | 103.5 |
| 40.0 | 100.2 | 103.5 | 102.7 | 102.7 |
| 45.0 | 99.6 | 102.6 | 101.9 | 101.9 |

Because the skin temperature test above could not in good conscience be repeated on a human subject without an outer pouch using the gel of Example 1, the following test was performed showing that the gels of Examples 1 and 7 retain and transmit heat energy in substantially the same way.

Gel packs containing the indicated gels were heated by methods described below and were folded in half. The temperature of the pack between the folded halves was recorded, as set forth in Table 2 below. As may be seen in this table, and especially in comparison of test samples E and F, the temperature profile of the gels of Examples 1 and 7 over time is substantially the same.

Test samples E and H contained the gel of Example 7. Test samples F, G, I and J each contained the gel of Example 1. Test samples E and F consisted of the inner bag without an outside sleeve and were heated by immersion in boiled water for seven minutes. Test samples G and I had the inner bag disposed within an outer pouch provided with capillaries, as described in Example 1. Test samples H and J had the inner bag disposed within a nonwoven sleeve that was made from Evolution TM Fabric, commercially available from Kimberly Clark Corporation (Dallas, Tex.). Test samples G and H were heated by immersion in boiled water for seven minutes. Test samples I and J were heated in a microwave oven at 40% power (defrost setting) for 2.5 minutes.

TABLE II

| Time (Minute) | Temperature °F. | | | | | |
|---|---|---|---|---|---|---|
| | E | F | G | H | I | J |
| 0.5 | 161.7 | 165.3 | 156.4 | 157.4 | 108.4 | 107.9 |
| 1.0 | 163.2 | 165.3 | 156.9 | 158.5 | 114.4 | 109.3 |
| 1.5 | 163.7 | 165.3 | 156.9 | 159.0 | 114.9 | 111.1 |
| 2.0 | 164.1 | 164.9 | 156.9 | 158.6 | 115.2 | 112.0 |
| 2.5 | 164.7 | 164.9 | 156.9 | 158.6 | 115.6 | 113.1 |
| 3.0 | 164.7 | 164.5 | 157.3 | 158.6 | 115.9 | 113.6 |
| 3.5 | — | 164.5 | — | 158.6 | — | 114.2 |
| 4.0 | 164.7 | 163.9 | 157.3 | 158.6 | 116.3 | 114.6 |
| 4.5 | — | — | — | 158.6 | — | 114.6 |
| 5.0 | 164.3 | 163.0 | 157.3 | 158.6 | 116.7 | 115.3 |
| 6.0 | 163.8 | 162.1 | 157.3 | 158.1 | 117.1 | — |
| 7.0 | 162.9 | 161.6 | 156.9 | 157.6 | 117.5 | — |
| 8.0 | — | — | 156.5 | — | 117.7 | — |
| 9.0 | — | — | 156.0 | — | 117.8 | — |
| 10.0 | — | — | 155.6 | — | 117.9 | — |
| 15.0 | — | — | 152.8 | — | 117.7 | — |
| 20.0 | — | — | 149.2 | — | 117.4 | — |
| 22.5 | — | — | — | — | — | 119.8 |
| 25.0 | — | — | 145.6 | — | 116.9 | — |
| 30.0 | — | — | 142.5 | — | 115.9 | — |
| 35.0 | — | — | 139.1 | — | 114.7 | — |
| 40.0 | — | — | 135.9 | — | 113.3 | — |
| 45.0 | — | — | 133.0 | — | 112.5 | — |

I claim:

1. A chemical thermal pack consisting of a flexible liquid tight inner bag containing a temperature-retaining composition and a non-water absorbant insulation sheet, said inner bag being disposed within an outer pouch constructed at least partially from a sheet of liquid impermeable material provided with capillaries each having a base in the plane of the sheet and an apex remote from said plane of said sheet.

2. The chemical thermal pack of claim 1 wherein said capillaries are tapered.

3. The chemical thermal pack of claim 2 wherein said capillaries are in the shape of frustum of a conical surface.

4. The chemical thermal pack of claim 3 wherein the apex has a diameter of from about 0.10 to about 2.54 mm. and the base has a diameter of about 0.15 to about 6.35 mm.

5. The chemical thermal pack of claim 4 wherein the apex has a diameter of from about 0.13 mm. to about 0.51 mm. and the base has a diameter of about 0.2 mm. to about 2.00 mm.

6. The chemical thermal pack of claim 4 wherein the apex has a diameter of about 0.35 mm. and the base has a diameter of about 0.5 mm.

7. The chemical thermal pack of claim 7 wherein said capillary has a base to apex distance of about 0.04 to about 2.0 mm.

8. The chemical thermal pack of claim 7 wherein said capillary has a base to apex distance of about 0.5 to about 1 mm.

9. The chemical thermal pack of claim 2 wherein said capillaries are in the shape of pyramidal tapered capillaries.

10. The chemical thermal pack of claim 9 wherein said pyramidal capillaries have triangular bases.

11. The chemical thermal pack of claim 9 wherein said pyramidal capillaries have square bases.

12. The chemical thermal pack of claim 1 wherein said capillaries are in an ordered arrangement with from about 5 to about 231 capillaries per square centimeter.

13. The chemical thermal pack of claim 1 wherein said capillaries are in an ordered arrangement with from about 50 to about 100 capillaries per square centimeter.

14. The chemical thermal pack of claim 1 wherein said outer pouch is sealed on all sides.

15. The chemical thermal pack of claim 1 that is mode from material that are microwaveable.

16. The chemical thermal pack of claim 1 that is made from material that are boilable.

17. The chemical thermal pack of claim 1 wherein said outer pouch is made from polyethylene.

18. The chemical thermal pack of claim 1 wherein said inner bag is made from a linear low density polyethylene/polyester laminate.

19. A chemical thermal pack consisting of a flexible liquid tight inner bag containing a temperature-retaining composition, said inner bag being disposed within an outer pouch constructed at least partially from a sheet of liquid impermeable material provided with capillaries each having a base in the plane of the sheet and an apex remote from said plane of said sheet.

20. The chemical thermal pack of claim 14 wherein at least one-half of said outer pouch is constructed from a sheet of liquid impermeable material provided with capillaries.

21. The chemical thermal pack of claim 14 wherein said outer pouch is constructed from an upper sheet of liquid impermeable material provided with capillaries and a lower sheet of liquid impermeable material that is not provided with capillaries.

22. A chemical thermal pack having a flexible liquid tight inner bag containing a temperature-retaining composition, said inner bag being disposed within an outer pouch constructed at least partially from a sheet of liquid impermeable material provided with capillaries each having a base in the plane of the sheet and an apex remote from said plane of said sheet, provided that no insulation material appears between said capillaries and said inner bag.

23. The chemical thermal pack of claim 21 which additionally contains an insulation sheet that is adjacent to and substantially covers the portion of the bag constructed from said lower sheet.

* * * * *

UNITED STATES PATENT AND TRADEMARK OFFICE
CERTIFICATE OF CORRECTION

PATENT NO. : 4,953,550

DATED : September 4, 1990

INVENTOR(S) : Wayne K. Dunshee

It is certified that error appears in the above-identified patent and that said Letters Patent is hereby corrected as shown below:

Col. 6, line 27, after the word "sheet" insert -- of --.

Cols. 7 & 8 Table I, under column D, "Ex. 1" should be -- Ex. 7 --.

Col. 9, Table II, in the first column "Minute" should be -- Minutes --.

Col. 9, line 53, "frustum" should be -- frustums --.

Col. 10, line 25, "mode" should be -- made --.

Col. 10, line 26, "material" should be -- materials --.

Col. 10, line 28, "material" should be -- materials --.

Signed and Sealed this

Twenty-ninth Day of September, 1992

Attest:

DOUGLAS B. COMER

*Attesting Officer*   *Acting Commissioner of Patents and Trademarks*